United States Patent [19]

Ayache et al.

[11] Patent Number: 4,795,638
[45] Date of Patent: Jan. 3, 1989

[54] THERMO SLIMMING COSMETIC COMPOSITION

[75] Inventors: Liliane Ayache, Paris; Jean-Pierre Laugier, Antony, both of France

[73] Assignee: L'Oreal, Paris, France

[21] Appl. No.: 798,415

[22] Filed: Nov. 15, 1985

[30] Foreign Application Priority Data

Nov. 16, 1984 [LU] Luxembourg ............... 85643

[51] Int. Cl.[4] ............................................. A61K 35/78
[52] U.S. Cl. ................................................. 424/195.1
[58] Field of Search ............................. 424/195.1, 78

[56] References Cited

FOREIGN PATENT DOCUMENTS 48622 5/1974 Australia .
2222088 10/1974 France .
2454803 11/1980 France .
2002233 2/1974 United Kingdom .
2092445 8/1982 United Kingdom .

OTHER PUBLICATIONS

Luxembourg Search Report.

*Primary Examiner*—John W. Rollins
*Attorney, Agent, or Firm*—Parkhurst, Oliff & Berridge

[57] ABSTRACT

A cosmetic composition is provided which can reduce or eliminate cellulite or fat build-ups on a human body. The composition includes at least one rubefacient, at least one oil soluble plant extract, and at least one volatile organo polysiloxane. The ingredients are contained in an oil base which can be of vegetable or animal origin, and mineral oil or even a synthetic oil or any mixture of these oils. The rubefacient substance is generally present in the compound in concentrations ranging from between 0.05 and 5% by weight. The substance which can be used as a rubefacient include capsicum extracts; nicotinic acid salts; nicotinic acid esters; and nicotinyl alcohols. The oil soluble plant extract can be a mixture of ivy, rosemary, ginseng, sage, arnica, Saint Johns wort, marigold, ruscus, ulmaria, orthosiphon and algae in any combination. The organo polysiloxane is generally in concentrations ranging between 10 and 85% by weight.

8 Claims, No Drawings

THERMO SLIMMING COSMETIC COMPOSITION

BACKGROUND OF THE INVENTION

The present invention relates to a cosmetic substance having an oil soluble plant extract base which, when applied to the skin, attempts to improve the appearance of the body by reducing cellulite and fat build-ups.

Many cosmetic composition have been proposed to try to eliminate the unattractive appearance of cellulite or fat build-up. These build-ups occur on various parts of the body but especially on the hips and thighs. The composition proposed in the past have not adequately eliminated the cellulite and fat build-ups.

SUMMARY OF THE INVENTION

This invention was developed in view of the foregoing background and to overcome the foregoing drawbacks.

It is accordingly an object of this invention to provide a composition which can reduce or eliminate cellulite or fat build-ups. Cellulite, as it is called, results from an accumulation of fatty materials and water imprisoned in a matrix made up of more or less water tight compartments. This matrix is comprised of elements of fundamental matter and more particularly of proteoglycons which are polymeric. The failure of the prior art compositions to eliminate cellulite is largely due to an inability of the active substances to penetrate the derma and reach the polymeric substances.

If some enzymes are capable of breaking up the long chains of polymeric substances, namely polysaccharides, into shorter chains with a release of water molecules, some plant extracts, using a different mechanism, can also obtain the same result if they can penetrate the barrier comprised of the derma and reestablish micro circulation.

The inventors have unexpectedly found that it is possible to combat cellulite and fat build-up effectively by combining oil soluble plant extracts which have a slimming action with a rubefacient which heats the skin upon application and thus accelerates the activation process of exchanges and superficial circulation. Thus optimal diffusion of the active ingredients of the composition toward their target, namely the unattractive bulges, is promoted.

DETAILED DESCRIPTION OF THE INVENTION

The above objects, features and advantages of the present invention will become more apparent from the description of the invention which follows which illustrates a preferred embodiment according to the present invention.

The subject of this invention is a thermo slimming cosmetic composition containing in an oily base: (1) at least one rubefacient; (2) at least one oil soluble plant extract from a plant chosen from the group comprising climbing ivy, arnica, rosemary, marigold, sage, ginseng; Saint Johns wort, ruscus, ulmaria, orthosiphon and algae; and (3) at least one volatile organo polysiloxane. The oil base of the composition in this invention is comprised preferably between 10 to 40% by weight of the cosmetic composition. This oil base can be an oil of vegetable or animal origin, a mineral oil or even a synthetic oil or mixtures of these oils.

Modified or unmodified oils of vegetable or animal origin could include, for example, oil of sweet almond, avocado oil, castor oil, olive oil, jojoba oil, perhydrosqualene, calophyllum, lanolin and its derivatives, sun flower oil, wheat germ oil, sesame oil, peanut oil, grape seed oil, soybean oil, colza oil, safflower oil, coconut oil, corn oil, walnut oil, karite butter, shorea-robusta oil, palm oil and peach stone oil.

Oils of mineral origin could include, for example, Vaseline oil. The synthetic oils could include, for example, ethyl and isopropyl palmitates, the alkyl myristates such as isopropyl, butyl myristate, and cetyl myristate, hexyl stearate, the capric and caprylic acid [decanoic and octanoic] triglycerides (for example the product sold under the trade name of Miglygol by Dynamite Nobel), cetyl ricinoleate, stearyl octanoate (oil of purcellin) and hydrogenated polyisobutene and waxes such as ozocerite [earthy-wax].

The oil base can also contain some compounds which are considered to be oily products, namely long chain alcohols, such as cetyl alcohol, stearyl alcohol, myristic alcohol, hydroxystearyl alcohol, oleic alcohol or isostearyl alcohol.

According to a preferred version of the invention, the oil base is comprised of vegetable oils either alone or in combination with synthetic esters and Vaseline oil.

The rubefacient substance which can also be defined as a hyperermic substance or a vazodiolator causes a slight warming of the skin, comparable to a massage, which enhances diffusion of the slimming active ingredients.

The rubefacient is generally present in the compound in concentrations ranging between 0.05 and 5% by weight.

Substances which can be used as a rubefacient include, for example, the following: capsicum extracts; nicotinic acid salts such as triethanolamine nicotinate; nicotinic acid esters such as for example methyl, ethyl, hexyl, phenyl, and benzyl nicotinate as well as alpha tocopherol nicotinate; nicotinyl alcohol and its organic acid esters such as for example nicotinyl tartarate or nicotinate.

Of course these rubefacients can be used in a mixture, for example, a mixture of methyl nicotinate and a capsicum extract standardized in capsaicin.

The oil soluble plant extract with slimming action is generally present in the mixture in concentrations ranging from 5 to 50% by weight of the total weight of the mixture.

Although it is possible to use a single oil soluble plant extract, it is nonetheless preferable in this invention to use a mixture of such extracts in that an effective complimentarity has been noted with regard to the slimming action. The following are preferred mixtures of oil soluble plant extracts: (a) ivy, rosemary and ginseng; (b) ivy, sage and arnica; (c) ivy, algae and rosemary; and (d) ivy, arnica, rosemary and ginseng.

The extract of climbing ivy (*Hedera Helix*) is obtained by prolonged soaking of the leaves in propylene glycol. The extract of arnica (*Arnica Montana*) is obtained by soaking of the arnica flower heads in glycol or in apricot seed oil. The extract of rosemary (*Rosmarinus officinalis N*) is obtained by prolonged soaking of the leaves in glycol or in apricot seed oil. The extract of marigold (*Calendula officinalis*) is obtained by prolonged soaking of the flowers in glycol or in apricot seed oil. The extract of sage (*Salvia officinalis L*) is obtained by prolonged soaking of the leaves in glycol or in apricot seed oil. The extract of ginseng (*Panax Ginseng*) is obtained by soaking of the ginseng roots in an eudermic neutral oil (mixture of Vaseline and apricot seed oil). The extract of Saint Johns wort (*Hypericum Perforatum*) is an extract obtained from the flowers by soaking in a eudermic neutral oil or in glycol. The extract of ruscus is obtained from rhizomes of ruscus (*Ruscus aculeatus*) which have been previously ground and extracted by means of a hydroalcoholic solution (a solution of water and alcohol) where the alcohol contains three to six carbon atoms (preferably by means of water saturated n-butanol). The extract of ulmaria (*Filipendula ulmaria L*) is obtained by prolonged soaking of the entire plant in an eudermic neutral oil or in isopropylmyristate. The extract of orthosiphon (*Ortosifon Stamincus Benth*) is obtained by prolonged soaking of the flower heads in an eudermic neutral oil. The extract of algae, for example *Fucus Vesiculosus*, is obtained by prolonged soaking of the entire plant in an oxyethylenated oil.

The volatile organo polysiloxane is in liquid form with a viscosity ranging between 2 and 10 CPS and is generally present in the cosmetic mixture involved in this invention in concentrations raging between 10 and 85% by weight. One could use alkyl polysiloxanes having the general formula

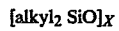

$$[alkyl_2 SiO]_x$$

where X would be between 4 and 5 and a representative alkyl would be a radical with one to two carbon atoms. These compounds could include the dimethyl polysiloxanes with four or five silicon atoms and in particular the compounds sold under the following trade names: Volatile Silicone 7207, Volatile Silicone VS7158 and Volatile Silicone VS7349 by Union Carbide; 245 Fluid, 345 Fluid, 344 Fluid and 244 Fluid by Dow Corning; and Rhodorsil 70045 V5 and Rhodorsil 70045 V2 by Rhone Poulenc. The organo polysiloxanes used in the mixtures involved in this invention enhance the action of the slimming active ingredients and avoid making the skin look greasy.

The cosmetic mixtures produced by this invention can also contain essential oils or perfumes in concentrations ranging between 0.05 and 2% by weight, camphor and/or menthol in concentrations ranging between 0.05 and 2% as well as antioxidants such as butyl hydroxyanisole or butyl hydroxytolulene in concentrations ranging between 0.01 and 0.1% as well as preservatives in concentrations ranging between 0.1 and 0.5%.

The mixtures in this invention would preferably be of the anhydrous type, for example in the form of an oil emulsion. They can however be in the form of a water in oil and would look like a cream or a lotion.

When the mixtures appear in the form of an emulsion, the oily phase of the emulsions would correspond to 20 to 80% by weight, the water phase being 20 to 40% and the emulsifying agent would be 5 to 30% by weight of the total weight of the emulsion.

The mixtures in this invention can also contain a foaming oil soluble tensioactive component in proportions ranging from 0.5 to 20% of the total weight of the mixture. This oil soluble tensioactive component comprises an anionic tensioactive agent whose acid function has been neutralized so as to make it oil soluble to which could potentially be added a non-ionic tensioactive agent and/or an alkanolamide.

The oil soluble tensioactive component preferred for this invention includes sulfated alcanols, sulfonated alkyl benzenes, carboxylated alkyl polyglycol ethers, carboxylated alkyl phenol polyglycol ethers, sulfated alkyl polyglycol ethers and sulfated alkyl phenyl polyglycol ethers, alone or in mixture, and neutralized by an amine or a mixture of amines, potentially in the presence of non-ionic tensioactive agents. The sulfated alkanols used in this invention are in particular saturated or non-saturated alkanols with a straight or branched chain comprising 10 to 22 carbon atoms and preferably 12 to 16 carbon atoms. These alkanols preferably include decyl alcohol, lauryl alcohol myristyl alcohol, cetyl alcohol, stearyl alcohol, oleyl alcohol as well as alcohols derived from fats or oils of natural origin such as $C_{12}$–$C_{14}$ alcohols, oleyl-cetyl alcohol, and $C_{12}$–$C_{18}$ fatty alcohols.

The sulfonated alkyl benzenes used in this invention preferably contain a straight chain alkyl residue with between 10 and 13 carbon atoms.

The sulfated alkyl polyglycol ethers preferably are alkanol addition compounds precipitated with 1 to 8 gram molecules, and, preferably, 1.5 to 3 gram molecules of ethylene oxide.

The sulfated alkyl phenol polyglycol ethers preferably contain a straight or branched chain alkyl residue with 7 to 12 carbon atoms and 5 to 10 gram molecules of ethylene oxide.

The carboxylated alkyl polyglycol ethers preferably used contain an alkyl residue with 12 to 18 carbon atoms and 2 to 20 gram molecules of ethylene oxide. The preferred carboxylated alkyl phenyl polyglycol ethers contain an alkyl residue with 7 to 12 carbon atoms and 2 to 20 gram molecules of ehtylene oxide.

The amines used for neutralizing the acid functions of the anionic tensioactive can include, for example the amines and the alkanolamines, or preferably methylamine, ethylamine, propylamine, isopropylamine, butylamine, hexylamine, ethanolamine, diethanolamine, triethanolamine, propanolamine, mono-, di-, or triisopropanolamine, dimethylaminoethanol, diethylamino ethanol, 2-amino-2-methyl-1,3-propanediol, 2-amino-2-methyl propanol, n,n-dimethylisopropanolamine, n-propylethanolamine, n-propyldiethanolamine, n,n-diethylaminoethoxyethanol, tertiarybutyldiethanolamine, used singly or in a mixture.

In using the mixtures of this invention one applies a sufficient quantity of the mixture to those parts of the body where trimming is desired. Light massage is used to enhance penetration and then one notes a sensation of warmth and observes a reddening of the surfaces treated.

The treatment consists of 1 to 3 applications per day and should be continued for about one month.

Tests carried out by the applicant have shown excellent slimming activity. Remote echography measurement was used to detect the thickness of the cellulite for these tests. These results have also been confirmed by anthropemetric measurements.

The invention is additionally illustrated in connection with the following Examples which are to be considered as illustrating of the present invention. It should be understood, however, that the invention is not limited to the specific details of the Examples.

EXAMPLE A

| THERMO SLIMMING OIL | |
|---|---|
| oil of sweet almond | 2 grams |

-continued

| THERMO SLIMMING OIL | |
|---|---|
| karite butter | 3 grams |
| stearyl octanoate [oil of purcellin | 5 grams |
| perhydrosqualene | 10 grams |
| methyl nicotinate | 0.5 grams |
| extract of climbing ivy | 10 grams |
| extract of arnica | 6 grams |
| extract of rosemary | 6 grams |
| extract of ginseng | 5 grams |
| preservative | 0.2 grams |
| aromatics | 1 gram |
| antioxidant | 0.2 grams |
| polysiloxane [poly organo siloxane] under the trade name of Volatile Silicone 7207 by Union Carbide | 100 grams |

In Example A, the methyl nicotinate can be successfully replaced by the same quantity of alpha tocopherol nicotinate or phenyl nicotinate.

EXAMPLE B

| THERMO SLIMMING BODY OIL | |
|---|---|
| triglycerides of octanoic and decanoic acids sold by the Dynamit Nobel Company under the trade name of Miglyol 812 | 15 grams |
| isopropyl palmitate | 10 grams |
| hazelnut oil | 5 grams |
| lanoline acetyl ester | 5 grams |
| capsicum | 0.5 grams |
| extract of climbing ivy | 8 grams |
| extract of sage | 8 grams |
| extract of ulmaria [meadow-sweet] | 10 grams |
| extract of fucus vesiculosus | 14 grams |
| preservative | 0.2 grams |
| perfume | 1 gram |
| antioxidant | 0.1 grams |
| polysiloxane [polyorgano siloxane] sold under the trade name of Rhodorsil 70045 V5 by the Rhone Poulenc Company | 15 grams |
| oil of Vaseline QSP | 100 grams |

EXAMPLE C

| THERMO SLIMMING BALM | |
|---|---|
| ozokerite [earth wax] | 10 grams |
| isopropyl palmitate | 10 grams |
| white petrolatum [cosmoline] | 15 grams |
| preservative | 0.2 grams |
| antioxidant | 0.3 grams |
| hexylnicotinate | 1.7 grams |
| extract of calendula | 5 grams |
| extract of fucus vesiculosus | 10 grams |
| extract of climbing ivy | 10 grams |
| extract of arnica | 5 grams |
| aromatics | 1 gram |
| polysiloxane [polyorgano siloxane] sold under the trade name of 245 Fluid by the Dow Corning Company | 25 grams |
| oil of Vaseline [petrolatum oil] QSP | 100 grams |

In Example C the hexylnicotinate can be successfully replaced by nicotinate nicotinyl or triethanolamine nicotinate.

EXAMPLE D

| THERMO SLIMMING FOAMING OIL | |
|---|---|
| extract of climbing ivy | 4 grams |
| extract of sage | 3 grams |
| extract of arnica | 4 grams |
| extract of rosemary | 3 grams |
| extract of ginseng | 3 grams |
| non-ionic tensioactive sold under the trade name Texapon W W 99 by the Henkel Company | 30 grams |
| preservative | 0.3 grams |
| antioxidant | 0.2 grams |
| methylnicotinate | 0.25 grams |
| aromatics | 1.5 grams |
| polysiloxane [polyorgano siloxane] sold under the trade name of volatile silicone VS 7158 by the Union Carbide Company | 17 grams |
| hydrogenated Polyisobutene | 13 grams |
| oil of petrolatum [Vaseline oil] QSP | 100 grams |

While the present invention has been disclosed in its preferred embodiments, it is to be understood that the invention is not limited thereto, and may be otherwise embodied within the scope of the following claims.

What is claimed is:

1. A thermo slimming cosmetic composition comprising in an oil base:
   at least one rubefacient substance;
   at least one oil soluble plant extract; and
   at least one volatile polysiloxane,
   said oil soluble plant extract being extracted from a plant selected from the group consisting of climbing ivy, arnica, rosemary, marigold, sage, ginseng, Saint Johns wort, ruscus, ulmaria, orthosiphon and algae, said oil soluble plant extract being present in a concentration ranging from 5 to 50% by weight of the total weight of the composition, said oil base constituting 10 to 40% by weight of the total weight of the composition, said rubefacient substance being present in a concentration ranging from approximately 0.05 to 5% by weight of the composition, said rubefacient substance being selected from the group consisting of capsicum, nicotinic acid salt, nicotinic acid ester, nicotinyl alcohol and an ester of nicotinyl alcohol, said polysiloxane being present in a concentration ranging from approximately 10 to 85% by weight, said polysiloxane being a dimethyl polysiloxane having 4 to 5 silicon atoms.

2. The thermo slimming cosmetic composition according to claim 1, further comprising perfumes in concentrations ranging from between 0.05 to 2% by weight, essential oils in concentrations ranging from between 0.05 and 2% by weight; camphor in concentrations ranging from 0.05 to 2% by weight, menthol in concentrations ranging from approximately 0.05 to 2% by weight, antioxidant agents in concentrations ranging from 0.01 to 0.1% by weight, and preservatives in concentrations ranging from 0.1 to 0.5% by weight.

3. The composition according to claim 1, wherein said dimethyl polysiloxane is cyclic.

4. The composition according to claim 1, wherein the oil soluble plant extract comprises at least one mixture selected from the group of mixtures consisting of:
   extracts of ivy, rosemary and ginseng;

extracts of ivy, sage and arnica;
extracts of ivy, algae and rosemary; and
extracts of ivy, rosemary, arnica and ginseng.

5. The composition according to claim 1, further comprising a non-ionic tensioactive component in concentrations ranging from 0.5 to 20%.

6. A procedure for treating cellulite and fatty build-ups on a body, comprising applying an effective amount of a thermo slimming cosmetic composition to the cellulite and fatty build-ups, said thermo slimming cosmetic composition comprising:
   an oil base;
   at least one rubefacient substance selected from the group consisting of capsicum, nicotinic acid salt, nicotinic acid ester, nicotinyl alcohol and an ester of nicotinyl alcohol;
   at least one oil soluble plant extract extracted from a plant selected from the group consisting of climbing ivy, arnica, rosemary, marigold, sage, ginseng, Saint Johns wort, ruscus, ulmaria, orthosiphon and algae; and
   at least one volatile dimethyl polysiloxane having 4 to 5 silicon atoms;
   wherein, said oil base constitutes 10 to 40% by weight of the total weight of the composition, said oil soluble plant extract constitutes 5 to 50% by weight of the total weight of the composition, said rubefacient substance constitutes 0.05 to 5% by weight of the total weight of the composition and said polysiloxane constitutes 10 to 85% by weight of the total weight of the composition.

7. The procedure according to claim 6, wherein said dimethyl polysiloxane is cyclic.

8. The procedure according to claim 6, wherein the treatment is carried out over a period of about one month with approximately one to three applications per day.

* * * * *